United States Patent
Chung

(10) Patent No.: US 9,603,581 B2
(45) Date of Patent: Mar. 28, 2017

(54) ULTRASONIC TRANSDUCER AND METHOD OF MANUFACTURING THE SAME

(71) Applicant: SAMSUNG ELECTRONICS CO., LTD., Suwon-si (KR)

(72) Inventor: Seok-whan Chung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 646 days.

(21) Appl. No.: 14/023,821

(22) Filed: Sep. 11, 2013

(65) Prior Publication Data

US 2014/0073927 A1    Mar. 13, 2014

(30) Foreign Application Priority Data

Sep. 11, 2012    (KR) .................. 10-2012-0100661

(51) Int. Cl.
   H01L 29/84    (2006.01)
   A61B 8/00    (2006.01)
   B06B 1/02    (2006.01)

(52) U.S. Cl.
   CPC .......... *A61B 8/4483* (2013.01); *B06B 1/0292* (2013.01); *H01L 29/84* (2013.01)

(58) Field of Classification Search
   CPC ...... B06B 1/0622; G10K 11/02; H04R 17/00; H01L 41/0926
   USPC .......................... 310/322, 324, 334, 335, 349
   See application file for complete search history.

(56) References Cited

U.S. PATENT DOCUMENTS

| | | | |
|---|---|---|---|
| 7,745,973 B2 | 6/2010 | Bayram et al. | |
| 7,759,839 B2 | 7/2010 | Huang | |
| 7,846,102 B2* | 12/2010 | Kupnik | B06B 1/0292 257/E21.002 |
| 2004/0190377 A1 | 9/2004 | Lewandowski et al. | |
| 2006/0238067 A1* | 10/2006 | Dausch | A61B 8/4483 310/311 |
| 2007/0228878 A1 | 10/2007 | Huang | |
| 2007/0299345 A1 | 12/2007 | Adachi et al. | |

(Continued)

FOREIGN PATENT DOCUMENTS

| | | |
|---|---|---|
| EP | 1810619 A1 | 7/2007 |
| KR | 10-2010-0057596 A | 5/2010 |

(Continued)

OTHER PUBLICATIONS

Written Opinion dated Dec. 19, 2013 issued by the International Searching Authority in counterpart International Application No. PCT/KR2013/008188 (PCT/ISA/237).

(Continued)

*Primary Examiner* — Shawki S Ismail
*Assistant Examiner* — Bryan Gordon
(74) *Attorney, Agent, or Firm* — Sughrue Mion, PLLC

(57) ABSTRACT

An ultrasonic transducer includes: a first electrode layer disposed on an upper substrate and a support; a second electrode layer which is disposed on a lower surface of the upper substrate and is separated from the first electrode layer; an upper electrode disposed on an upper surface of a membrane to contact an upper surface of the first electrode layer; a trench formed through the upper electrode, the membrane, the support, and the upper substrate; and a pad substrate disposed under the upper substrate and including bonding pads that electrically connect to the first and second electrode layers, respectively.

17 Claims, 14 Drawing Sheets

(56) References Cited

U.S. PATENT DOCUMENTS

| | | | |
|---|---|---|---|
| 2008/0089179 A1* | 4/2008 | Matsumoto | A61B 8/12 367/140 |
| 2008/0197751 A1* | 8/2008 | Huang | B06B 1/0292 310/311 |
| 2009/0140606 A1 | 6/2009 | Huang | |
| 2009/0204004 A1* | 8/2009 | Adachi | A61B 8/12 600/459 |
| 2011/0115333 A1* | 5/2011 | Ezaki | B06B 1/0292 310/300 |
| 2011/0316387 A1* | 12/2011 | Togasaki | B06B 1/0622 310/334 |
| 2012/0086087 A1 | 4/2012 | Fitzpatrick | |
| 2012/0150041 A1* | 6/2012 | Kim | B06B 1/0292 600/459 |

FOREIGN PATENT DOCUMENTS

| | | |
|---|---|---|
| KR | 10-2011-0025447 A | 3/2011 |
| KR | 10-2011-0079096 A | 7/2011 |

OTHER PUBLICATIONS

Jin, et al. "Characterization of One-Dimensional Capacitive Micromachined Ultrasonic Immersion Transducer Arrays", IEEE Transactions on Ultrasonics, Ferroelectrics, and Frequency Control, May 1, 2001, vol. 48, Issue No. 3, pp. 750-760, XP 011438295.

Zhuang, et al., "Integration of trench-isolated through-wafer interconnects with 2d capacitive micromachined ultrasonic transducer arrays", Sensors and Actuators A, Jul. 3, 2007, vol. 138, Issued No. 1, pp. 221-229, XP 022138384.

Communication issued Apr. 28, 2016, issued by the European Patent Office in counterpart European Patent Application No. 13837761.9.

* cited by examiner

ULTRASONIC TRANSDUCER AND METHOD OF MANUFACTURING THE SAME

CROSS-REFERENCE TO RELATED APPLICATION

This application claims the priority from the Korean Patent Application No. 10-2012-0100661, filed on Sep. 11, 2012, in the Korean Intellectual Property Office, the disclosure of which is incorporated herein in its entirety by reference.

BACKGROUND

1. Field

Apparatuses and methods consistent with exemplary embodiments relate to ultrasonic transducers and methods of manufacturing the same, and more particularly, to capacitive micromachined ultrasonic transducers (CMUTs) and methods of manufacturing the same.

2. Description of the Related Art

Ultrasonic transducers convert electric signals to ultrasonic signals, or vice versa. An example of the ultrasonic transducer may be a micromachined ultrasonic transducer (MUT). The MUT may be a piezoelectric micromachined ultrasonic transducer (PUMP), a CMUT, and magnetic micromachined ultrasonic transducer (MMUT). Among these, the CMUT drew attention in the fields of medical image diagnostic devices and sensors. The CMUT has a structure in which the elements that are basic driving units are arranged two dimensionally. When the CMUT is driven, an undesirable crosstalk, i.e., interference, between the elements may be generated when vibration of driven elements is transferred to other adjacent elements.

SUMMARY

Exemplary embodiments may address at least the above problems and/or disadvantages and other disadvantages not described above. Also, exemplary embodiments are not required to overcome the disadvantages described above, and an exemplary embodiment may not overcome any of the problems described above.

One or more of exemplary embodiments provide CMUTs and methods of manufacturing the CMUTs.

According to an aspect of an exemplary embodiment, an ultrasonic transducer comprises: an upper substrate; a support disposed on the upper substrate and comprising a cavity; a membrane disposed on the support and covering the cavity; a first electrode layer disposed on the upper substrate; a second electrode layer electrically connected to a lower surface of the upper substrate and is separated from the first electrode layer; and a trench formed by penetrating through the upper substrate and a lower insulating layer.

The first electrode layer may be disposed to cover a surface of the upper substrate and a surface of the support.

The ultrasonic transducer may further comprise a via hole and an upper electrode. The first electrode layer may be disposed to cover an inner wall of the via hole, and the upper electrode may be disposed on the membrane and electrically connected to the first electrode layer. The ultrasonic transducer may further a bridge membrane, the bridge membrane may be connected to the membrane the membrane may comprise silicon, and the support may comprise silicon oxide.

The ultrasonic transducer may further comprise an upper insulating layer and the upper and lower insulating layer may be formed respectively on an upper surface and the lower surface of the upper substrate, and the lower insulating layer may be patterned so that the second electrode layer contacts the lower surface of the upper substrate.

The ultrasonic transducer may further comprise a first upper pad and a second upper pad, and the first and second upper pads may be disposed on an upper surface of the pad substrate and bonded respectively to the first electrode layer and the second electrode layer.

The first and second electrode layers may include at least one of gold (Au) and copper (Cu), and the first and second upper pads may include at least one of Au, Cu, and tin (Sn).

The plurality of bonding pads may further include a first lower pad and a second lower pad that are disposed on a lower surface of the pad substrate and electrically connected to the first upper pad and the second upper pad.

According to another aspect of an exemplary embodiment, a method of manufacturing an ultrasonic transducer comprises: preparing a first wafer comprising a first lower substrate, a first insulating layer, and a membrane that are sequentially stacked in this order; forming a support on the membrane; preparing a second wafer comprising an upper substrate and a second insulating layer formed on a first surface of the upper substrate; bonding the second insulating layer to the support to form a cavity; forming a first electrode layer on the upper substrate; forming a second electrode layer on a second surface of the upper substrate; forming a lower trench through the upper substrate, the second insulating layer, and the support; removing the first lower substrate and the first insulating layer; and forming an upper trench that is connected to the lower trench, in the upper electrode and the membrane.

The first wafer may be a silicon on insulator (SOI) wafer. The support may be formed by forming a third insulating layer on the membrane and patterning the third insulating layer. The method may further comprise processing the upper substrate to have a predetermined thickness after the bonding of the second insulating layer.

The forming of the first and second electrode layers may comprise: forming a via hole in the upper substrate and the second insulating layer; forming a fourth insulating layer on an inner wall of the via hole, a portion of the membrane exposed by the via hole, and the second surface of the upper substrate; patterning the fourth insulating layer to partially expose the second surface of the upper substrate; and forming the first electrode layer on the fourth insulating layer in the via hole, and forming the second electrode layer on the fourth insulating layer and a portion of an exposed second surface of the upper substrate.

The method of manufacturing an ultrasonic transducer may further comprise forming an upper electrode on the membrane to contact the first electrode layer, and the forming of the upper electrode may comprise: forming a groove exposing an upper surface of the first electrode layer by etching the membrane and the fourth insulating layer on the via hole; and forming the upper electrode on an inner wall of the groove and the membrane.

The method of manufacturing an ultrasonic transducer may further comprise bonding a pad substrate on which bonding are formed to the first and second electrode layers, and the plurality of bonding pads may comprise a first upper pad and a second upper pad that are disposed on an upper surface of the pad substrate and bonded respectively to the first electrode layer and the second electrode layer. The first and second electrode layers may be respectively bonded to the first and second upper pads by a eutectic bonding method.

According to another aspect of an exemplary embodiment, an ultrasonic transducer comprises: an upper substrate; a support structure disposed on the upper substrate, the support structure comprising a cavity; a membrane disposed on the support; a bridge membrane connected to the membrane in the cavity and separated from the support structure; a first electrode layer disposed on the upper substrate; a second electrode layer electrically connected to a lower surface of the upper substrate and is separated from the first electrode layer; and an upper electrode disposed on the membrane and the bridge membrane to contact the first electrode layer.

According to another aspect of an exemplary embodiment, a method of manufacturing an ultrasonic transducer comprises: preparing a first wafer comprising a first lower substrate, a first insulating layer, and a membrane that are sequentially stacked in this order; forming a first support and a bridge support on the membrane; exposing the first insulating layer by etching the membrane inside the bridge support; preparing a second wafer comprising a second lower substrate, a second insulating layer, and a second upper substrate that are sequentially stacked; bonding the second upper substrate to the first support and the bridge support; removing the second lower substrate and the second insulating layer; forming a second support and a bridge membrane by forming a third support on the second upper substrate and patterning the second upper substrate exposed by the third support; preparing a third wafer comprising an upper substrate and a third insulating layer formed on a first surface of the upper substrate, and bonding the third insulating layer to the third support; forming a first electrode layer in the upper substrate; and forming a second electrode layer on a second surface of the upper substrate.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
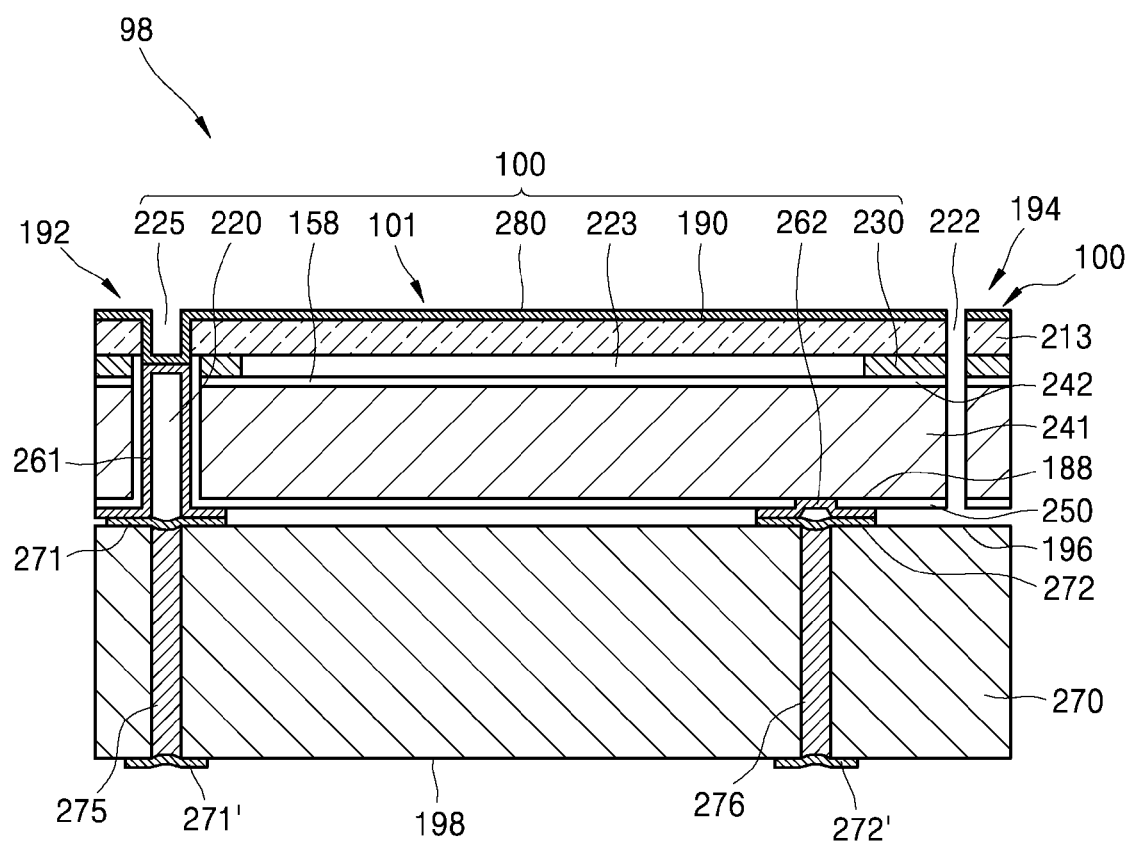
FIG. 1 is a cross-sectional view of a CMUT according to an exemplary embodiment.

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

Exemplary embodiments may be embodied in many different forms and should not be construed as being limited. In the drawings, the thicknesses of layers and regions are exaggerated for clarity. It will also be understood that when a layer is referred to as being "on" another layer or substrate, it can be directly on the other layer or substrate, or intervening layers may also be present. For example, in exemplary embodiments described below, materials forming each of layers are examples, and thus, other materials may be also used.

FIG. 1 is a cross-sectional view of a CMUT according to an exemplary embodiment.

Referring to FIG. 1, the CMUT 98 includes a plurality of elements 100, each including at least one cavity 223. For example, the plurality of elements 100 is separated from each other by trenches for preventing crosstalk between the elements 100. In FIG. 1, only one element 101 and only one trench 222 are shown for convenience of description. Further, FIG. 1 exemplary shows that the element 101 includes one cavity 223; however, the element 101 may include a plurality of cavities.

The element 101 of the CMUT 98 includes an upper substrate 241, i.e., a conductive substrate, a support 230 and a membrane 213 disposed on the upper substrate 241, and a pad substrate 270 disposed under the upper substrate 241. The upper substrate 241 may function as a lower electrode. For example, the upper substrate 241 may be a low resistive silicon substrate; however, an exemplary embodiment is not limited thereto. An upper insulating layer 242 may be formed on a first surface 158 of the upper substrate 241. The upper insulating layer 242 may include, for example, a silicon oxide; however, an exemplary embodiment is not limited thereto.

The support 230, in which the cavity 223 is formed, is disposed on the upper insulating layer 242. The support 230 may include, for example, silicon oxide; however, an exemplary embodiment is not limited thereto. The membrane 213 is disposed on the support 230 and covers the cavity 223. The membrane 213 may be formed of, for example, silicon; however, an exemplary embodiment is not limited thereto. A via hole 220 is formed to penetrate through the upper substrate 241, the upper insulating layer 242, and the support 230. An insulating layer, for example, a silicon oxide, may be disposed on an inner wall of the via hole 220.

A first electrode layer 261 is disposed to cover the inner walls and an upper portion of the via hole 220. A lower insulating layer 250 may be formed on a second surface 188 of the upper substrate 241. The lower insulating layer 250 is patterned to expose a portion of the second surface 188 of the upper substrate 241, and a second electrode layer 262 is formed to contact the exposed portion of the second surface 188 of the upper substrate 241. The first and second electrode layers 261 and 262 may include a conductive material. For example, the first and second electrode layers 261 and 262 may include at least one of gold (Au) and copper (Cu). These materials are examples, and the first and second electrode layers 261 and 262 may be formed of various materials.

An upper electrode 280 is disposed on an upper surface 190 of the membrane 213 so as to contact the first electrode layer 261. A groove 225 is formed in the membrane 213 proximate the via hole 220, on a first side 192 of the element 101. The upper electrode 280 extends along inner walls and a bottom portion of the groove 225 to contact the first electrode layer 261. For example, the trench 222 penetrating through the upper electrode 280, the membrane 213, the support 230, the upper insulating layer 242, the upper substrate 241, and the lower insulating layer 250 are formed distal to the groove 225 and the via hole 220, on a second side 194 of the element 101. The trench 222 prevents crosstalk between the elements 101.

The pad substrate 270 is disposed under the upper substrate 241. The pad substrate 270 may be, for example, a silicon substrate; however, an exemplary embodiment is not limited thereto. A plurality of bonding pads that are electrically connected to the first and second electrode layers 261 and 262 are formed on the pad substrate 270. The bonding pads include a first upper pad 271 and a second upper pad 272 that are formed on an upper surface 196 of the pad substrate 270 and respectively bonded to the first and second electrode layers 261 and 262. The first and second upper pads 271 and 272 may include a conductive material. For example, the first and second upper pads 271 and 272 may include at least one of Au, Cu, and tin (Sn). In more detail, the first and second upper pads 271 and 272 may include an Au/Sn layer. However, an exemplary embodiment is not limited thereto, and the first and second upper pads 271 and 272 may include various other materials.

The first electrode layer 261 and the first upper pad 271, and the second electrode layer 262 and the second upper pad 272 may be bonded to each other by a eutectic bonding method, respectively. For example, if the first electrode layer 261 is formed of an Au layer and the first upper pad 271 is formed of an Au/Sn layer, when the first electrode layer 261 and the first upper pad 271 are bonded to each other by the eutectic bonding, an Au—Sn eutectic alloy may be formed at an interface between the first electrode layer 261 and the first upper pad 271. However, the bonding of the first electrode layer 261 and the first upper pad 271 and the bonding of the second electrode layer 262 and the second upper pad 272 may be performed using other bonding methods, besides the eutectic bonding method.

First and second lower pads 271' and 272' that are electrically connected to the first and second upper pads 271 and 272, respectively, may be formed on a lower surface 198 of the pad substrate 270. A first conductive filling 275 electrically connects the first upper pad 271 and the first lower pad 271' to each other, and a second conductive filling 276 electrically connects the second upper pad 272 and the second lower pad 272' to each other. The first and second lower pads 271' and 272' may include a conductive material that is the same as that of the first and second upper pads 271 and 272; however, an exemplary embodiment is not limited thereto.

FIGS. 2 through 12 are diagrams illustrating a method of manufacturing a CMUT, according to an exemplary embodiment.

Figure 2:
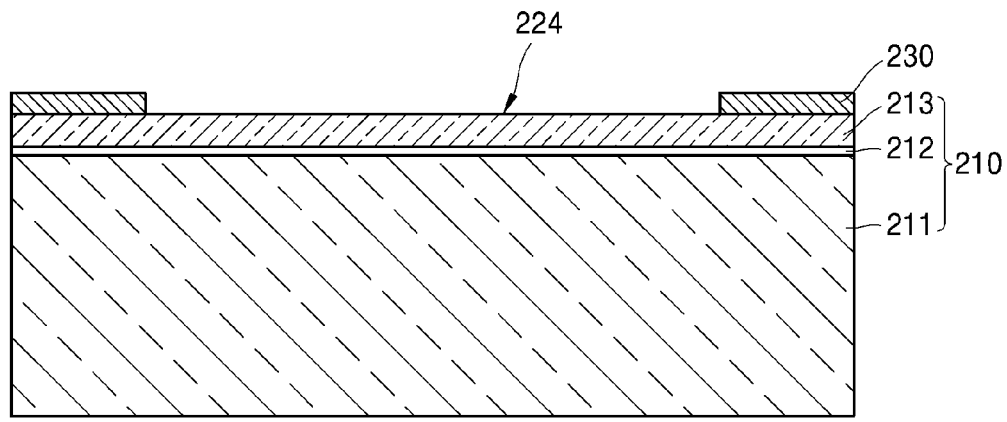
FIGS. 2, 3, 4, 5, 6, 7, 8, 9, 10, 11, and 12 are diagrams illustrating a method of manufacturing a CMUT, according to an exemplary embodiment.

Referring to FIG. 2, a first wafer 210 is prepared. The first wafer 210 includes a first lower substrate 211, a first insulating layer 212, and a first upper substrate, i.e., membrane 213 that are sequentially stacked in this order. The first wafer 210 may be, for example, an SOI wafer. Next, a support 230 is formed on the membrane 213. The support 230 may be formed by forming an insulating layer including, for example, an oxide material, on the membrane 213, and etching the insulating layer by using an etching mask formed of photoresist, to expose a portion of the first surface 224 of the membrane 213. The etching may be performed by an inductively coupled plasma-reactive ion etching (ICP-RIE); however, an exemplary embodiment is not limited thereto. For example, the photoresist used as the etching mask and residue generated due to the etching process are primarily removed by an oxygen ($O_2$) plasma etching method, and then, secondarily removed by using a solution, as for example, acetone and/or sulfuric acid.

Figure 3:
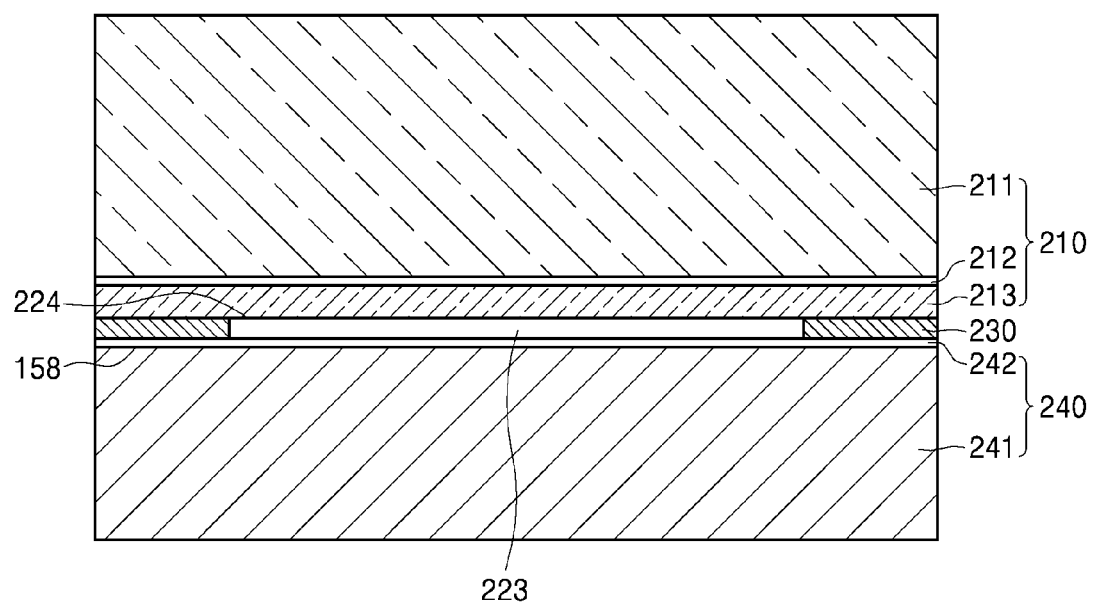

Referring to FIG. 3, a second wafer 240 is prepared. The second wafer 240 includes an upper substrate 241 and an upper insulating layer 242 formed on a first surface 158 of the upper substrate 241. The upper substrate 241 may include, for example, conductive silicon. A low resistive wafer, including a low resistive silicon substrate and a silicon oxide layer, may be used as the second wafer 240. Next, the upper insulating layer 242 of the second wafer 240 is bonded to the support 230 so as to cover a cavity 223. In FIG. 3, the structure shown in FIG. 2 is turned over, and the second wafer 240 is bonded on the support 230. The upper insulating layer 242 and the support 230 may be bonded to each other by a silicon direct bonding (SDB) method.

Figure 4:
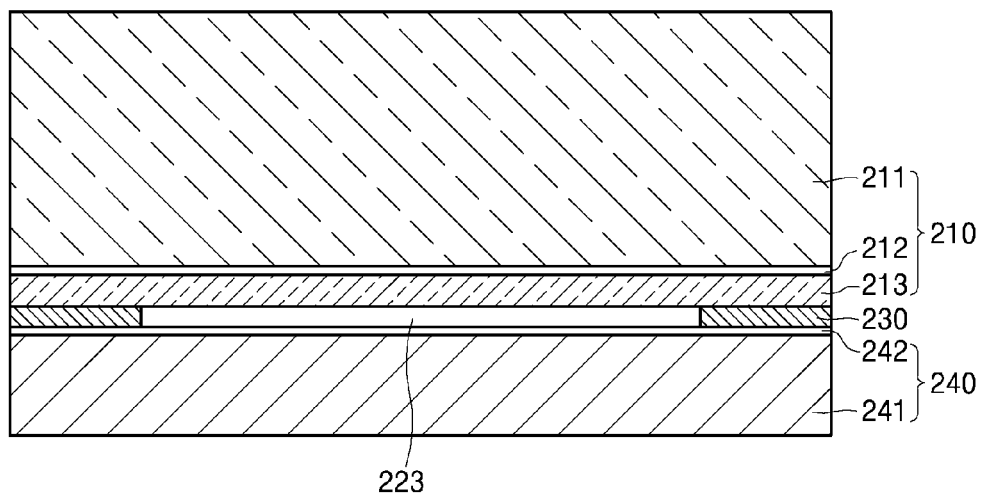

Referring to FIG. 4, the upper substrate 241 may be processed to have a desired thickness (for example, about 20 μm), for example, by a grinding process or a polishing process. The upper substrate 241 may be processed to be thinner in order to easily form a via hole 220 connecting an upper electrode 280 to a pad substrate 270 formed under the second wafer 240, as described in detail below.

Figure 5:
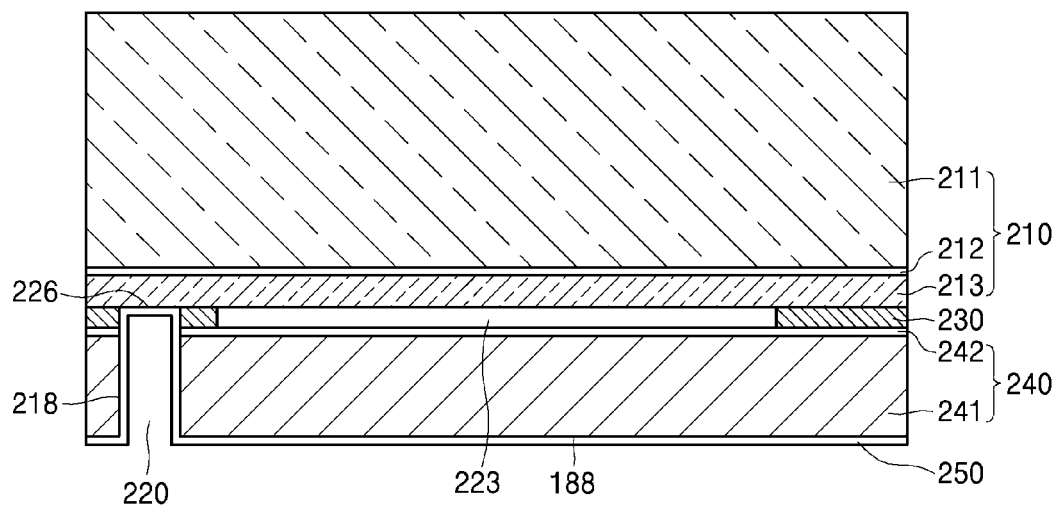

Referring to FIG. 5, the via hole 220 penetrating through the upper substrate 241, the upper insulating layer 242, and the support 230 is formed. The via hole 220 may be formed by etching the upper substrate 241 by a deep RIE method, and by etching the upper insulating layer 242 and the support 230 by an ICP etching method. For example, a fourth insulating layer, i.e., the lower insulating layer 250 is formed on inner walls 218 of the via hole 220, a first portion 226 of the membrane 213 exposed through the via hole 220, and a second surface 188 of the upper substrate 241. The lower insulating layer 250 may include, for example, an oxide material formed by wet etching the lower surface of the upper substrate 241 to a thickness of about 1 μm. The lower insulating layer 250 is formed to insulate a first electrode layer 261 and a second electrode layer 262 from each other.

Figure 6:
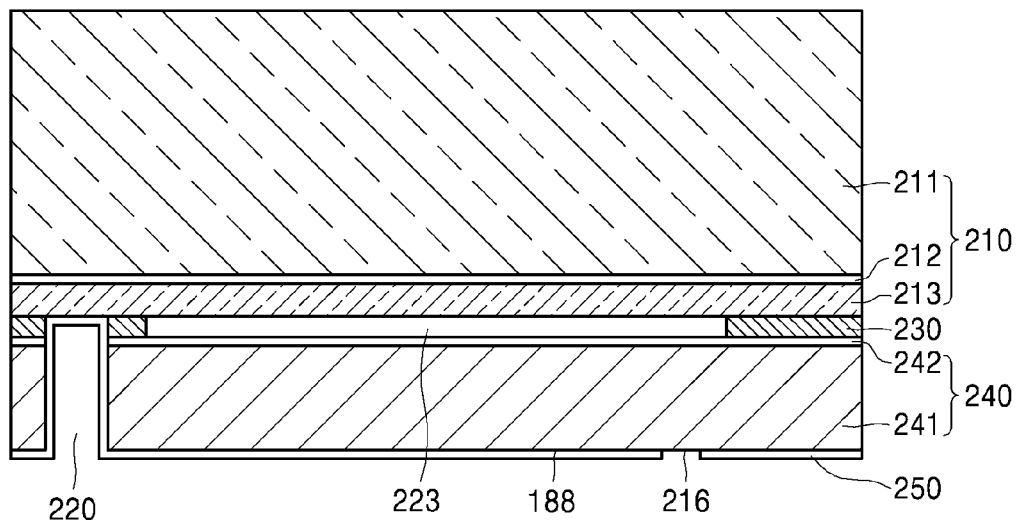

Referring to FIG. 6, the lower insulating layer 250 formed on the second surface 188 of the upper substrate 241 is wet-etched, for example, to partially expose a portion 216 of the second surface 188 of the upper substrate 241.

Figure 7:
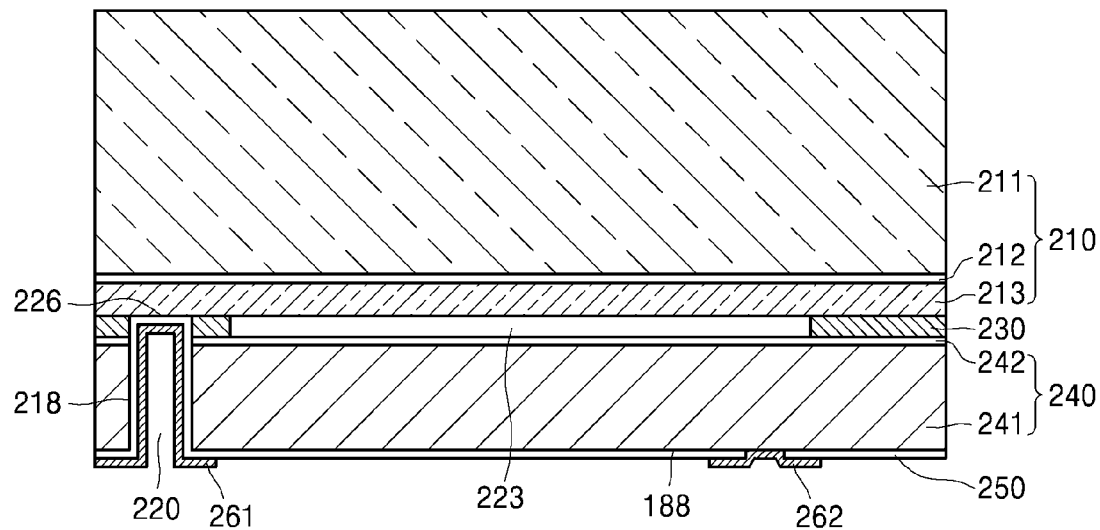

Referring to FIG. 7, the first electrode layer 261 is formed on the inner walls of the via hole 220, i.e., on the lower insulating layer 250 covering inner walls 218 of the via hole 220 and the first portion 226 of the membrane 213. The second electrode layer 262 is formed to contact the exposed portion 216 of the second surface 188 of the upper substrate 241. The first electrode layer 261 may extend onto the second surface 188 of the upper substrate 241. The first and second electrode layers 261 and 262 may be formed by depositing an electrode material such as Cr/Au on the lower insulating layer 250 by a sputtering process, and wet etching the electrode material. The second electrode layer 262 may be separated from the first electrode layer 261.

Figure 8:
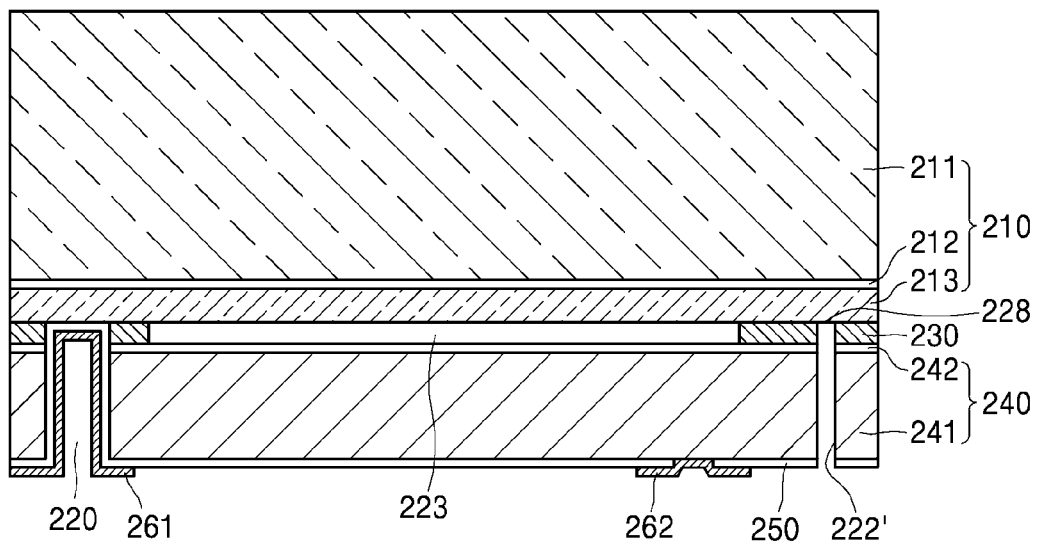

Next, as shown in FIG. 8, a lower trench 222' is formed. The lower trench 222' may be formed by etching the lower insulating layer 250, the upper substrate 241, the second insulating layer, i.e., the upper insulating layer 242, and the support 230 until a second portion 228 of the membrane 213 is exposed.

Figure 9:
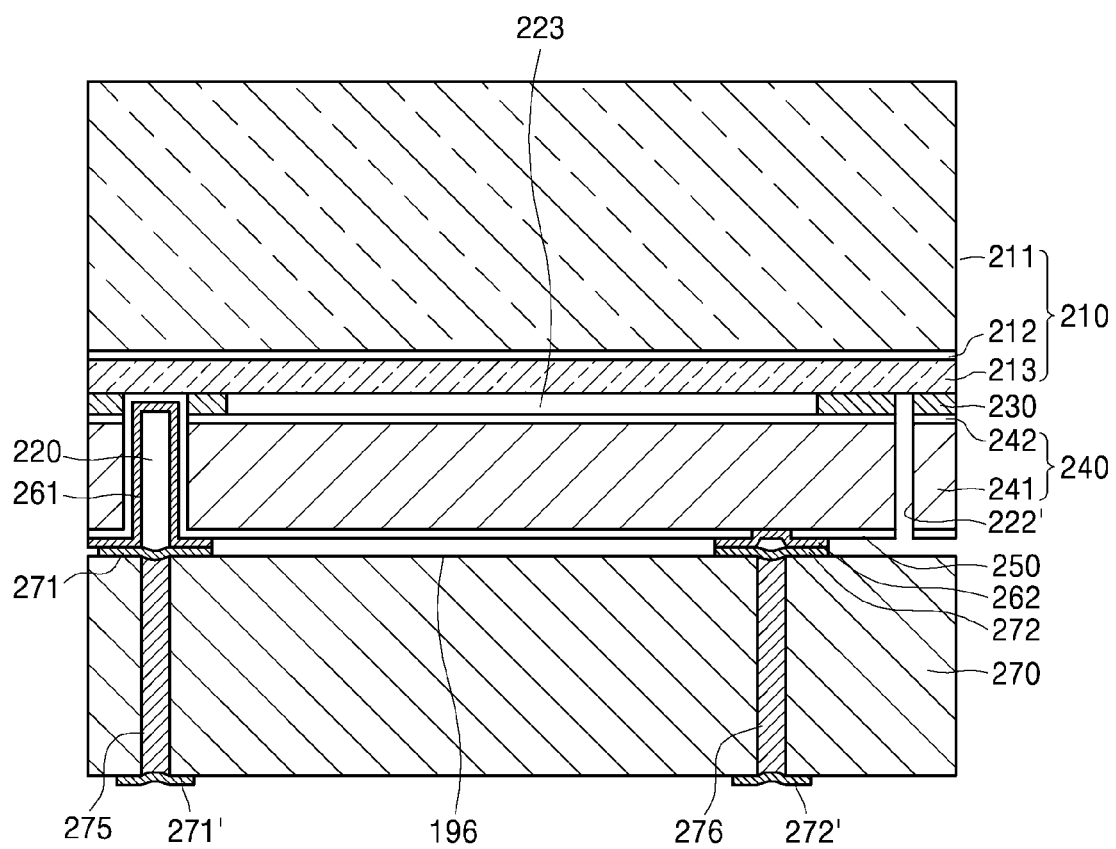

Referring to FIG. 9, a plurality of bonding pads is formed on the pad substrate 270 and bonded to the first and second electrode layers 261 and 262. The bonding pads include a first upper pad 271 and a second upper pad 272 that are disposed on an upper surface 196 of the pad substrate 270 and respectively bonded to the first and second electrode layers 261 and 262.

Figure 10:
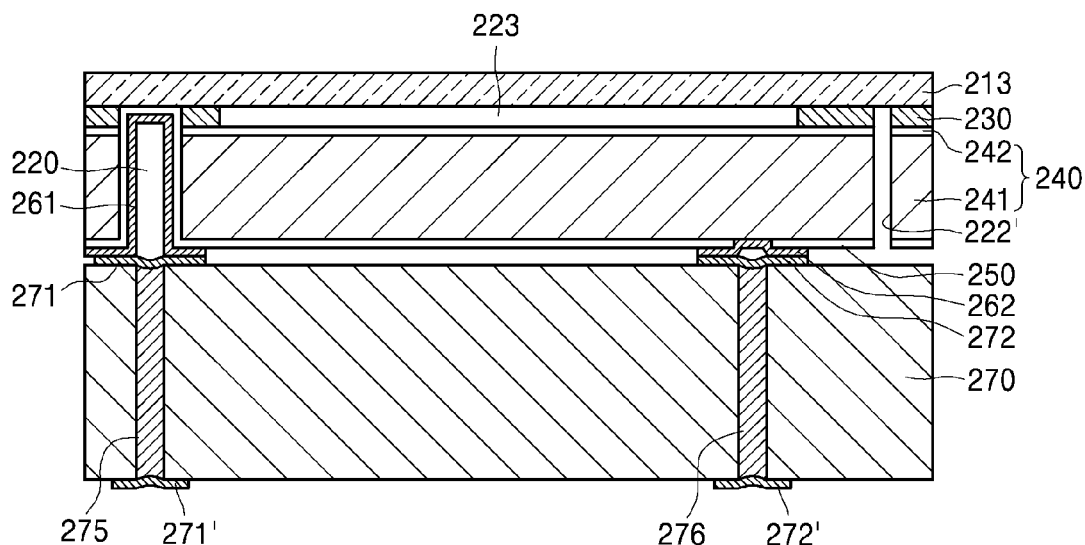

Referring to FIG. 10, the first lower substrate 211 and the first insulating layer 212 are removed. The first lower substrate 211 may be removed by, for example, a grinding process or a plasma etching process, and the first insulating layer 212 may be removed by an oxide ICP dry etching method that shows a high etch selectivity with respect to silicon.

Figure 11:
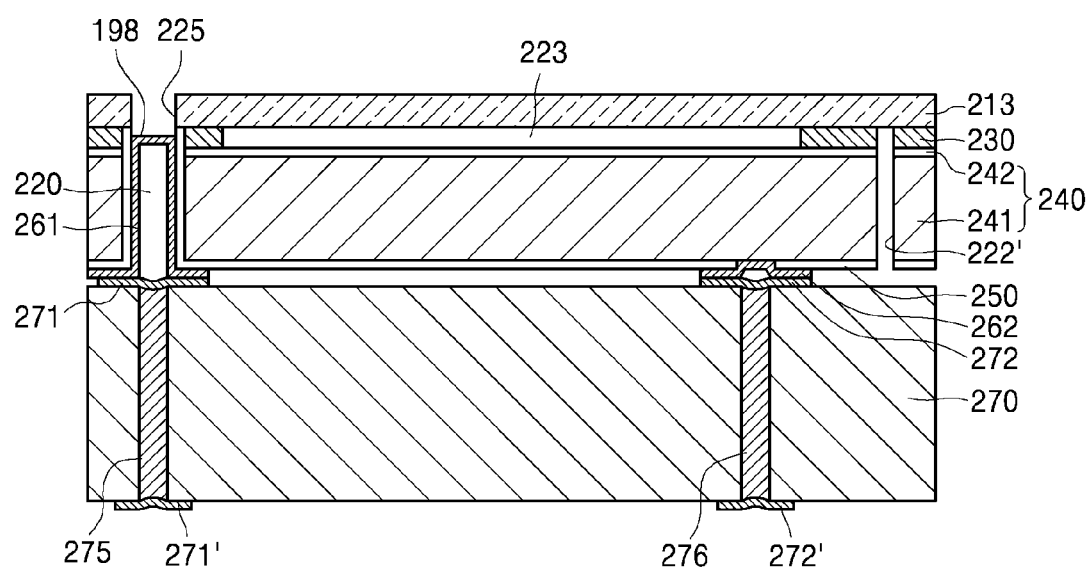

Referring to FIG. 11, a groove 225 is formed by etching the membrane 213 and the lower insulating layer 250 above the via hole 220 to expose the upper surface 198 of the first electrode layer 261.

Figure 12:
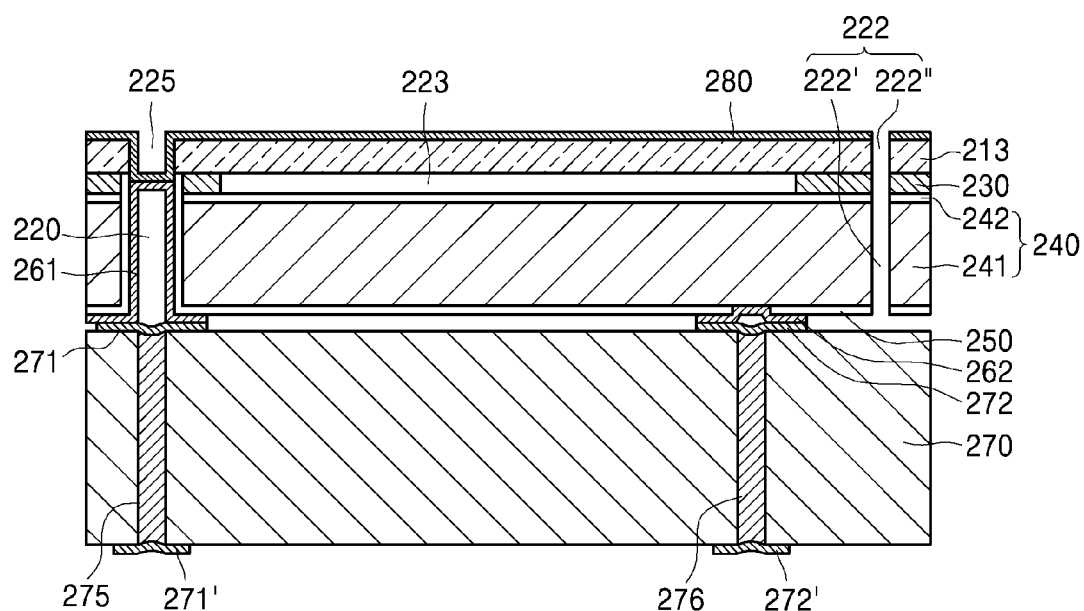

Referring to FIG. 12, an upper electrode 280 is formed on inner walls forming a periphery of the groove 225, including inner walls of the membrane 213 and the upper surface 198 of the first electrode layer 261. Accordingly, the upper electrode 280 may contact the upper surface 198 of the first electrode layer 261. The upper electrode 280 may be formed by depositing Al to a thickness of about 2000 Å. Further, an upper trench 222" is formed by etching the upper electrode 280 and the membrane 213 to connect to the lower trench 222'. Accordingly, a trench 222 for preventing crosstalk is formed through the upper electrode 280, the membrane 213, the support 230, the upper insulating layer 242, the upper substrate 241, and the lower insulating layer 250.

Figure 13:
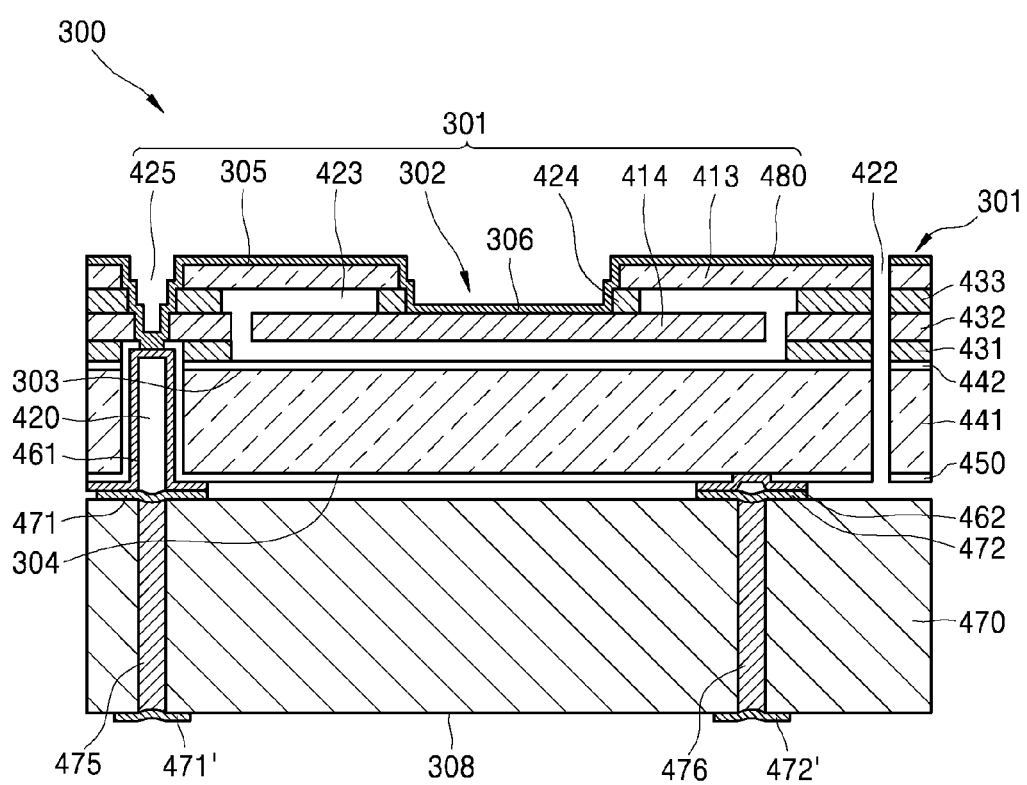
FIG. 13 is a cross-sectional view of a CMUT according to an exemplary embodiment.

FIG. 13 is a cross-sectional view of a CMUT according to an exemplary embodiment.

Referring to FIG. 13, the CMUT 300 includes a plurality of elements 301, each of which includes a cavity 423. For example, the plurality of elements 301 is separated from each other by trenches for preventing crosstalk between the elements 301. In FIG. 13, only one element 302 and only one trench 422 are shown for convenience of description. Further, FIG. 13 exemplary shows that the element 302 includes one cavity 423; however, the element 302 may include a plurality of cavities.

Referring to FIG. 13, the element 302 of the CMUT 300 includes an upper substrate 441, a support structure disposed on the upper substrate 441 and including the cavity 423, a membrane 413 disposed on the support structure, a bridge membrane 414 formed in the cavity 423 to be connected to the membrane 413, and a pad substrate 470 disposed under the upper substrate 441. The upper substrate 441 may function as a lower electrode. For example, the upper substrate 441 may be a low resistive silicon substrate; however, an exemplary embodiment is not limited thereto. An upper insulating layer 442 may be formed on a first surface 303 of the upper substrate 441. The upper insulating layer 442 may include, for example, a silicon oxide; however, an exemplary embodiment is not limited thereto.

The support structure, including the cavity 423, is disposed on the upper insulating layer 442. The support structure may include a third support 431, a second support 432, and a first support 433 that are sequentially stacked on the upper insulating layer 442. The first, second, and third supports 433, 432, and 431 may include, for example, a silicon oxide; however, an exemplary embodiment is not limited thereto. The membrane 413 is disposed on the support structure to cover the cavity 423. The membrane 413 may be formed of, for example, silicon; however, an exemplary embodiment is not limited thereto. The bridge membrane 414 is disposed in the cavity 423 and is separated from the support. The bridge membrane 414 may be disposed apart from the second support 432 at a plane at the same level as that of the second support 432. For example, the bridge membrane 414 may be supported by a bridge support 424 that is connected to the membrane 413.

A via hole 420 is formed to penetrate through the upper substrate 441, the upper insulating layer 442, and the third support 431. An insulating material, such as a silicon oxide, may be disposed on an inner wall of the via hole 420.

A first electrode layer 461 is disposed on the inner wall and an upper portion of the via hole 420. A lower insulating layer 450 may be formed on a second surface 304 of the upper substrate 441. The lower insulating layer 450 is patterned to partially expose the second surface 304 of the upper substrate 441, and a second electrode layer 462 is formed to contact the exposed second surface 304 of the upper substrate 441. The first and second electrode layers 461 and 462 may include a conductive material. For example, the first and second electrode layers 461 and 462 may include at least one of Au and Cu. However, an exemplary embodiment is not limited to the above examples, and the first and second electrode layers 461 and 462 may include various other materials.

An upper electrode 480 is disposed on upper surfaces 305, 306 of the membrane 413 and the bridge membrane 414, respectively, to contact the first electrode layer 461. A groove 425 exposing an upper surface of the first electrode layer 461 is formed in the membrane 413, the first support 433, and second support 432 above the via hole 420. The upper electrode 480 extends onto an inner wall of the groove 425 to contact the first electrode layer 461. For example, the trench 422 penetrating through the upper electrode 480, the membrane 413, the first, second, and third supports 433, 432, and 431, the upper insulating layer 442, the upper substrate 441, and the lower insulating layer 450 is formed to be apart from the via hole 420. The trench 422 prevents crosstalk between the elements 301.

The pad substrate 470 is disposed under the upper substrate 441. The pad substrate 470 may be, for example, a silicon substrate; however, an exemplary embodiment is not limited thereto. A plurality of bonding pads that are electrically connected to the first and second electrode layers 461 and 462 are formed on the pad substrate 470. The bonding pads include a first upper pad 471 and a second upper pad 472 that are formed on an upper surface of the pad substrate 470 and respectively bonded to the first and second electrode layers 461 and 462. The first and second upper pads 471 and 472 may include a conductive material. For example, the first and second upper pads 471 and 472 may include at least one of Au, Cu, and tin (Sn). In more detail, the first and second upper pads 471 and 472 may include an Au/Sn layer. However, an exemplary embodiment is not limited thereto, and the first and second upper pads 471 and 472 may include various other materials. The first electrode layer 461 and the first upper pad 471, and the second electrode layer 462 and the second upper pad 472 may be bonded to each other in a eutectic bonding method. For example, if the first electrode layer 461 is an Au layer and the first upper pad 471 is an Au/Sn layer, when the first electrode layer 461 and the first upper pad 471 are bonded to each other by the eutectic bonding method, an Au—Sn eutectic alloy may be generated at an interface between the first electrode layer 461 and the first upper pad 471. However, the bonding of the first electrode layer 461 and the first upper pad 471 and the bonding of the second electrode layer 462 and the second upper pad 472 may be performed by other bonding methods, besides the eutectic bonding method.

A first lower pad 471' and a second lower pad 472' that are electrically connected to the first and second upper pads 471 and 472, respectively, may be formed on the lower surface 308 of the pad substrate 470. A first conductive filling 475 for electrically connecting the first upper pad 471 and the first lower pad 471' is formed in the pad substrate 470, and a second conductive filling 476 for electrically connecting the second upper pad 472 and the second lower pad 472' is formed in the pad substrate 470. The first and second lower pads 471' and 472' may include the same conductive material as that of the first and second upper pads 471 and 472; however, an exemplary embodiment is not limited thereto.

FIGS. 14 through 27 are diagrams illustrating a method of manufacturing a CMUT, according to an exemplary embodiment.

Figure 14:
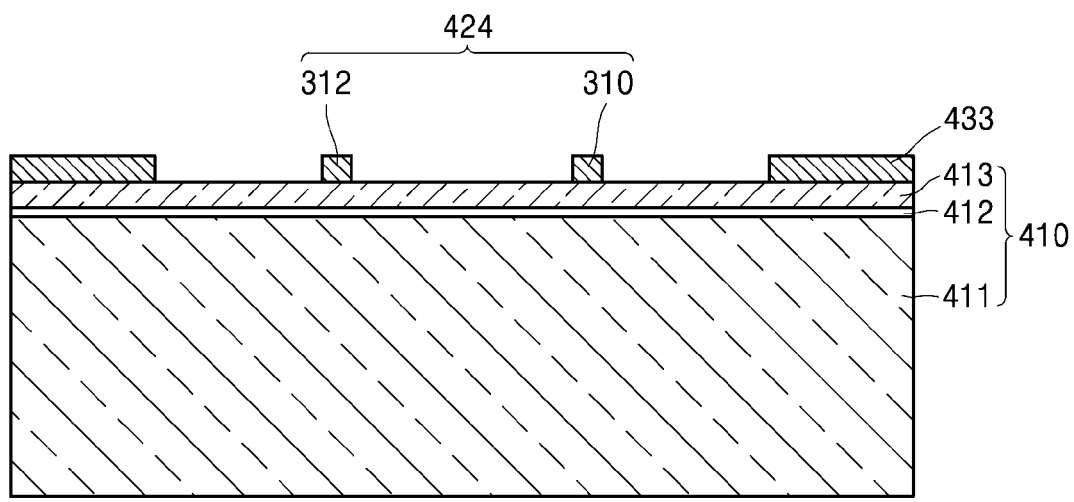
FIGS. 14, 15, 16, 17, 18, 19, 20, 21, 22, 23, 24, 25, 26, and 27 are diagrams illustrating a method of manufacturing a CMUT, according to an exemplary embodiment.

Referring to FIG. 14, a first wafer 410 is prepared. The first wafer 410 includes a first lower substrate 411, a first insulating layer 412, and a first upper substrate, i.e., membrane 413 that are sequentially stacked in this order. The first wafer 410 may be, for example, an SOI wafer. For example, a first support 433 and a bridge support 424 are formed on the membrane 413. The first support 433 and the bridge support 424 may be formed by forming a fourth insulating layer including, for example, an oxide material, on the membrane 413 and etching the fourth insulating layer. The etching process may be, for example, an ICP-RIE method; however, an exemplary embodiment is not limited thereto. The bridge support 424 is disposed at the same plane as that of the first support 433 and apart from the first support 433 and may include a first bridge element 310 and a second bridge element 312.

Figure 15:
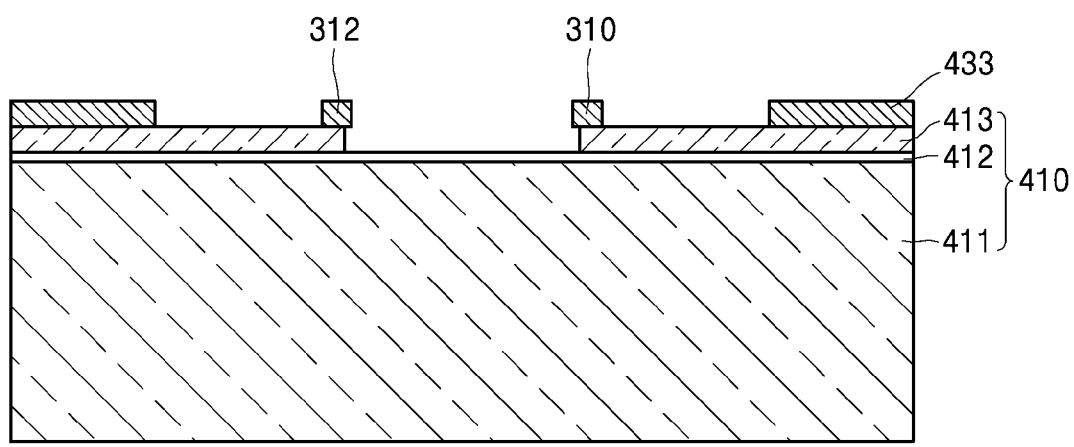

Referring to FIG. 15, the membrane 413 located inside the first and second bridge elements 310 and 312 is etched to expose the first insulating layer 412.

Figure 16:
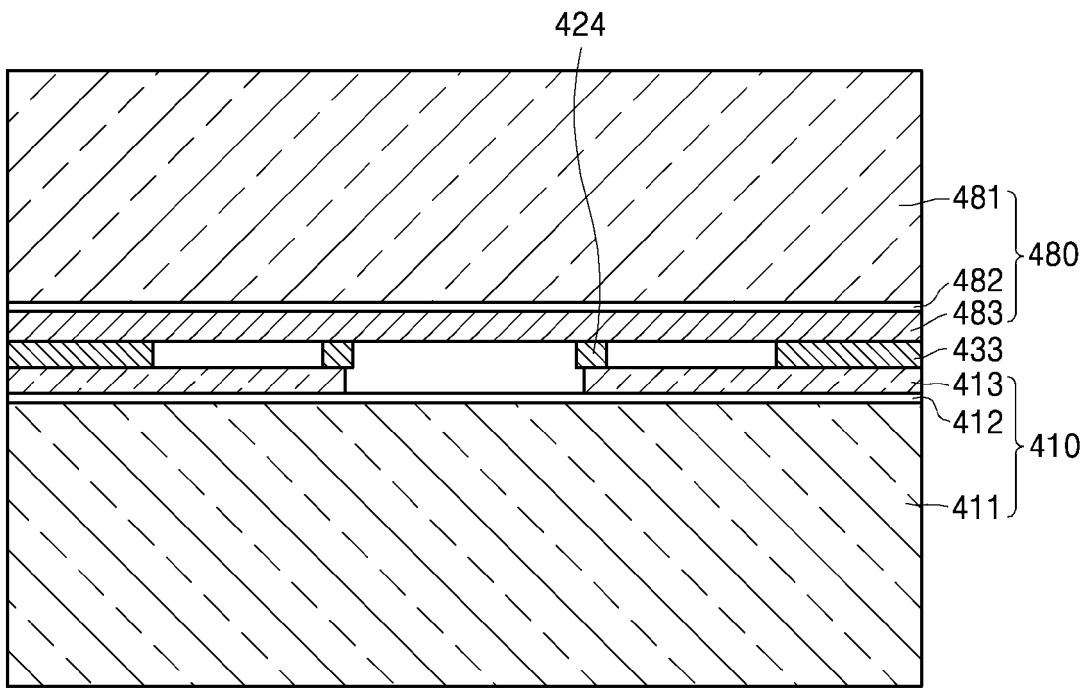

Referring to FIG. 16, a second wafer 480 is prepared. The second wafer 480 includes a second lower substrate 481, a second insulating layer 482, and a second upper substrate 483 that are sequentially stacked, and the second upper substrate 483 is bonded onto the first support 433 and the bridge support 424. The second wafer 480 may be, for example, an SOI wafer. Bonding between the second upper substrate 483 and the first support 433 and the bridge support 424 may be performed by an SDB method.

Figure 17:
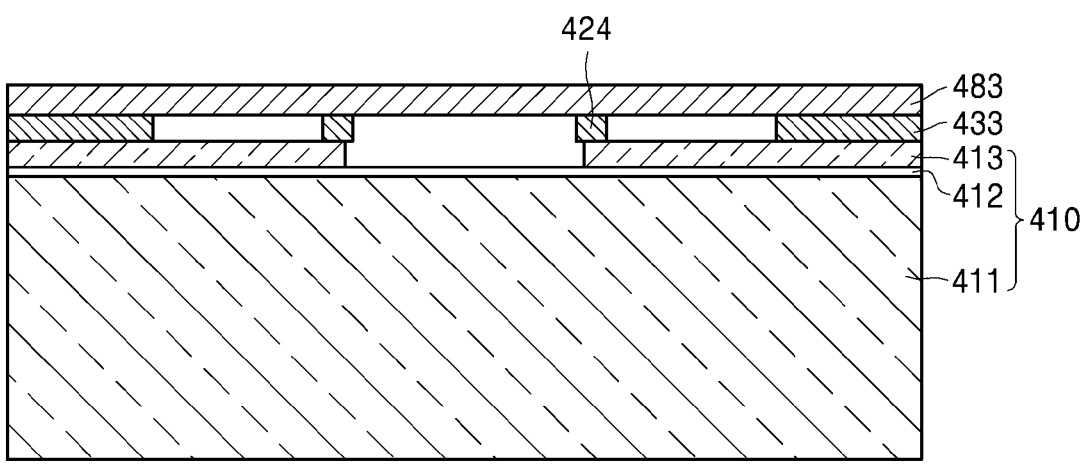

Referring to FIG. 17, the second lower substrate 481 and the second insulating layer 482 are removed. The second lower substrate 481 may be removed by, for example, a grinding process or a plasma etching process, and the second insulating layer 482 may be removed by, for example, an ICP dry etching process.

Figure 18:
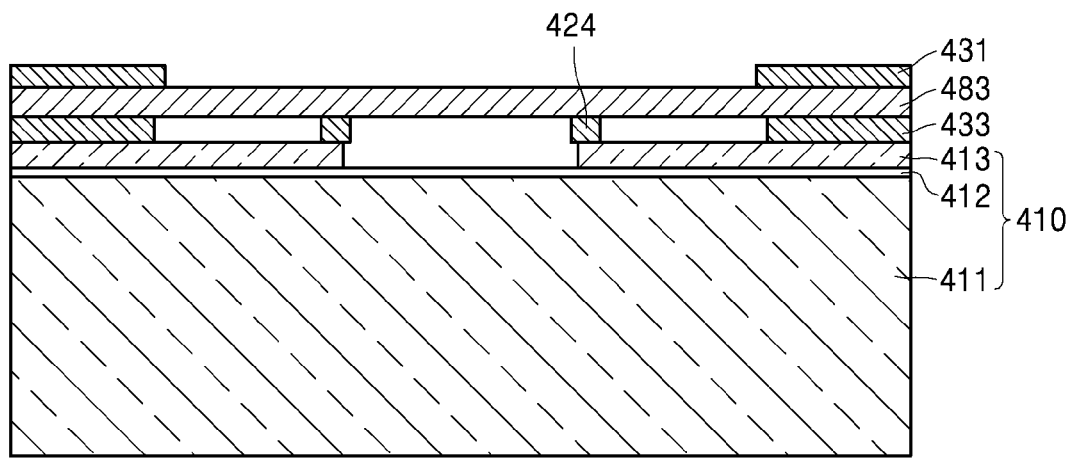

Referring to FIG. 18, a third support 431 is formed on the second upper substrate 483. The third support 431 may be formed by forming a fifth insulating layer including, for example, an oxide material, on the second upper substrate 483, and etching the fifth insulating layer.

Figure 19:
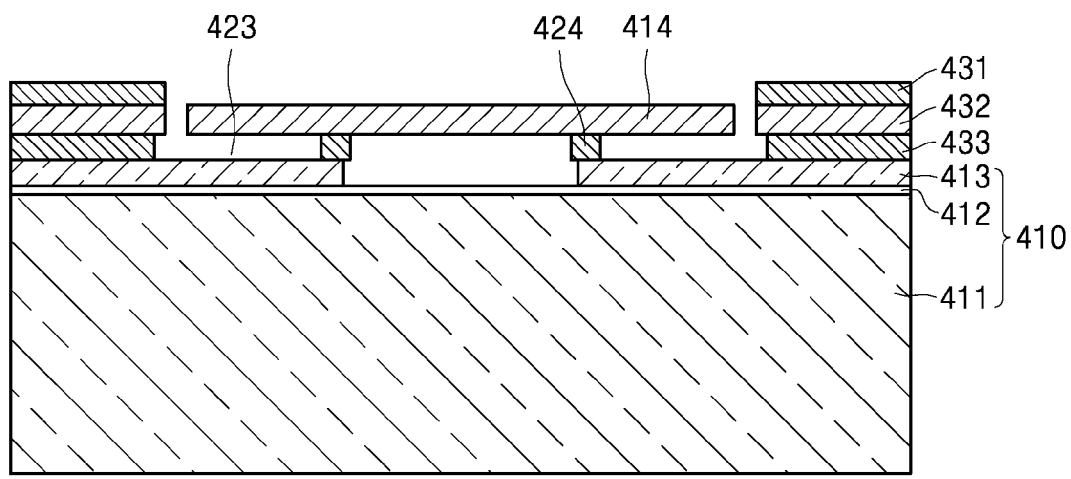

Referring to FIG. 19, the second upper substrate 483 that is exposed through the third support 431 is etched to form a second support 432 and a bridge membrane 414. Thus, the bridge membrane 414 is formed at the same level as that of the second support 432 and apart from the second support 432. The bridge membrane 414 is supported by the bridge support 424 that is connected to the membrane 413. The first, second, and third supports 433, 432, and 431 are sequentially stacked on the membrane 413 and form the cavity 423. The bridge membrane 414 that is connected to the membrane 413 is disposed in the cavity 423 and is separated from first, second, and third supports 433, 432, and 431.

Figure 20:
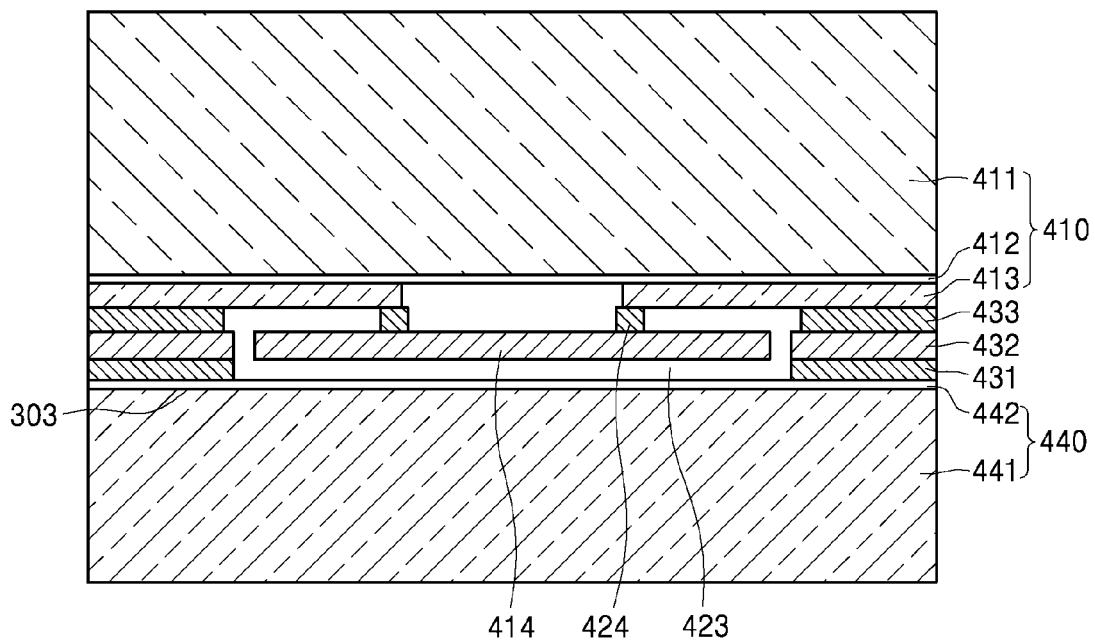

Referring to FIG. 20, a third wafer 440 is prepared. The third wafer 440 includes an upper 441, i.e., a third substrate, and an upper insulating layer 442, i.e., a third insulating layer, formed on a first surface 303 of the upper substrate 441. The upper substrate 441 may include, for example, conductive silicon. The third wafer 440 may be, for example, a low resistive wafer including a low resistive silicon substrate and a silicon oxide layer. For example, the upper insulating layer 442 of the third wafer 440 is bonded to the third support 431 so as to cover the cavity 423.

In FIG. 20, the structure shown in FIG. 19 is turned over, and the third support 431 is bonded to the upper insulating layer 442 of the third wafer 440. Bonding of the upper insulating layer 442 and the third support 431 may be performed by, for example, an SDB method.

Figure 21:
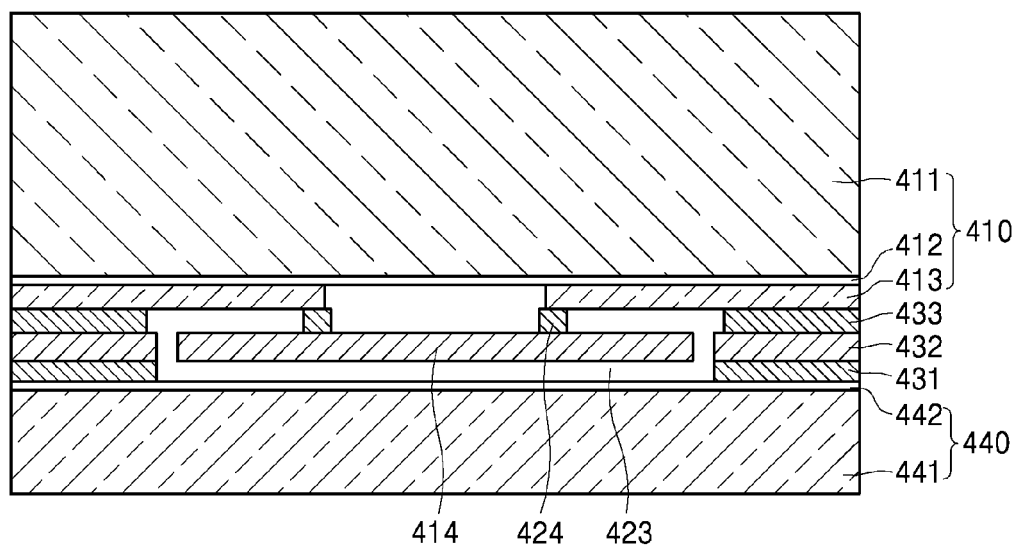

Referring to FIG. 21, the upper substrate 441 may be processed to have a desired thickness, for example, about 20 μm, for example, by using a grinding and a polishing process.

Figure 22:
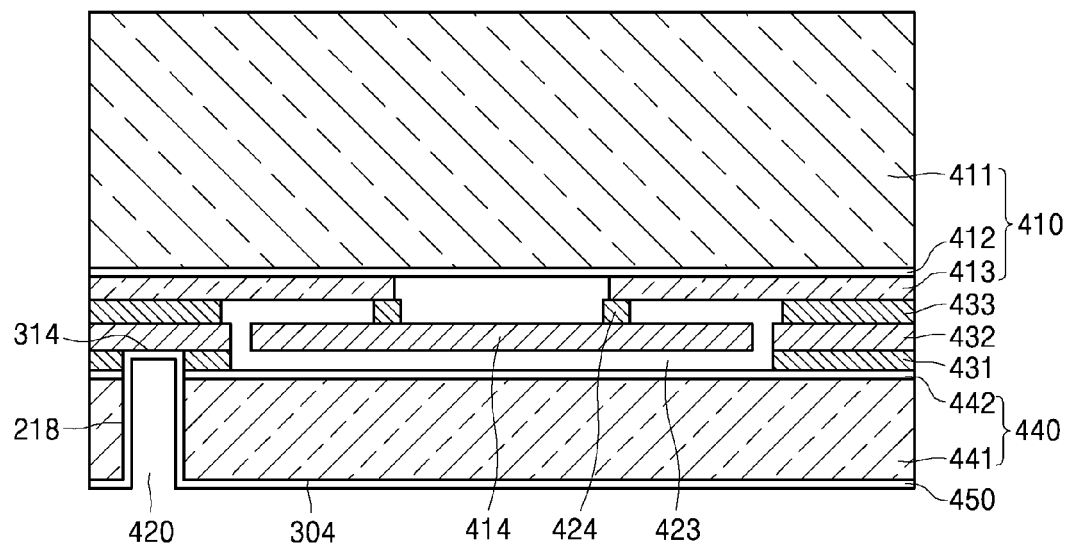

Referring to FIG. 22, a via hole 420 penetrating through the upper substrate 441, the upper insulating layer 442, and the third support 431 is formed. The via hole 420 may be formed by, for example, etching the upper substrate 441 by using a deep RIE method and etching the upper insulating layer 442 and the third support 431 by using an ICP etching method. Next, a lower insulating layer 450. i.e., a sixth insulating layer, is formed on an inner wall of the via hole 420, a portion 314 of the second support 432 exposed through the via hole 420, and a second surface 304 of the upper substrate 441. The lower insulating layer 450 is formed to insulate a first electrode layer 461 and a second electrode layer 462 from each other.

Figure 23:
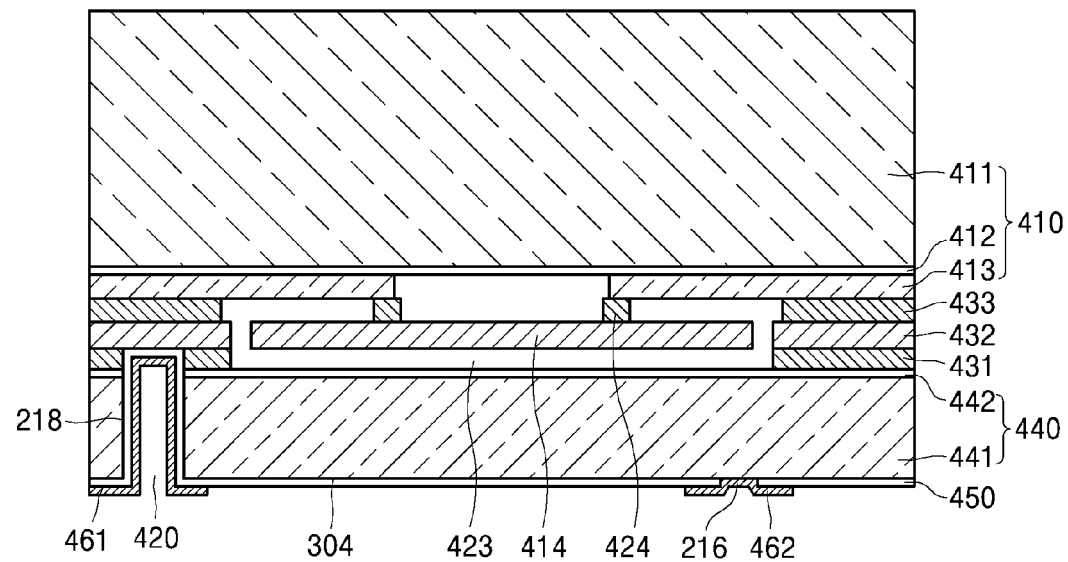

Referring to FIG. 23, the lower insulating layer 450 formed on the second surface 304 of the upper substrate 441 is etched to partially expose a portion 216 of the second surface 304 of the upper substrate 441. For example, the first electrode layer 461 is formed on the inner wall of the via hole 420, and the second electrode layer 462 is formed to contact the exposed portion of the second surface 304 of the upper substrate 441. The first electrode layer 461 may extend onto the second surface 304 of the upper substrate 441. The first and second electrode layers 461 and 462 may be formed by forming an electrode material layer, such as Cr/Au layer, on the lower insulating layer 450 and etching the electrode material layer. The second electrode layer 462 is separated from the first electrode layer 461.

Figure 24:
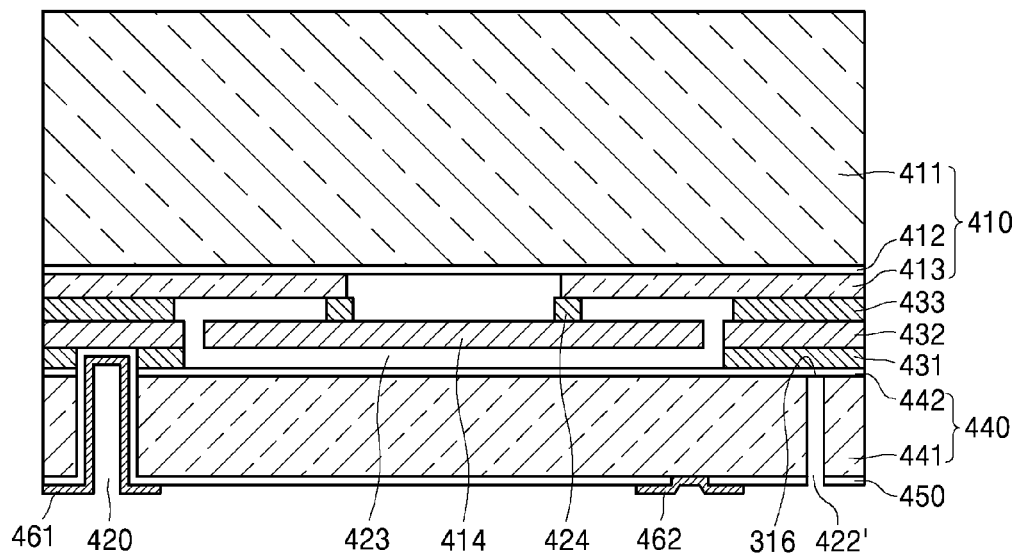

Referring to FIG. 24, a lower trench 422' is formed. The lower trench 422' may be formed by etching the lower insulating layer 450 and the upper substrate 441 until a portion 316 of the upper insulating layer 442 is exposed.

Figure 25:
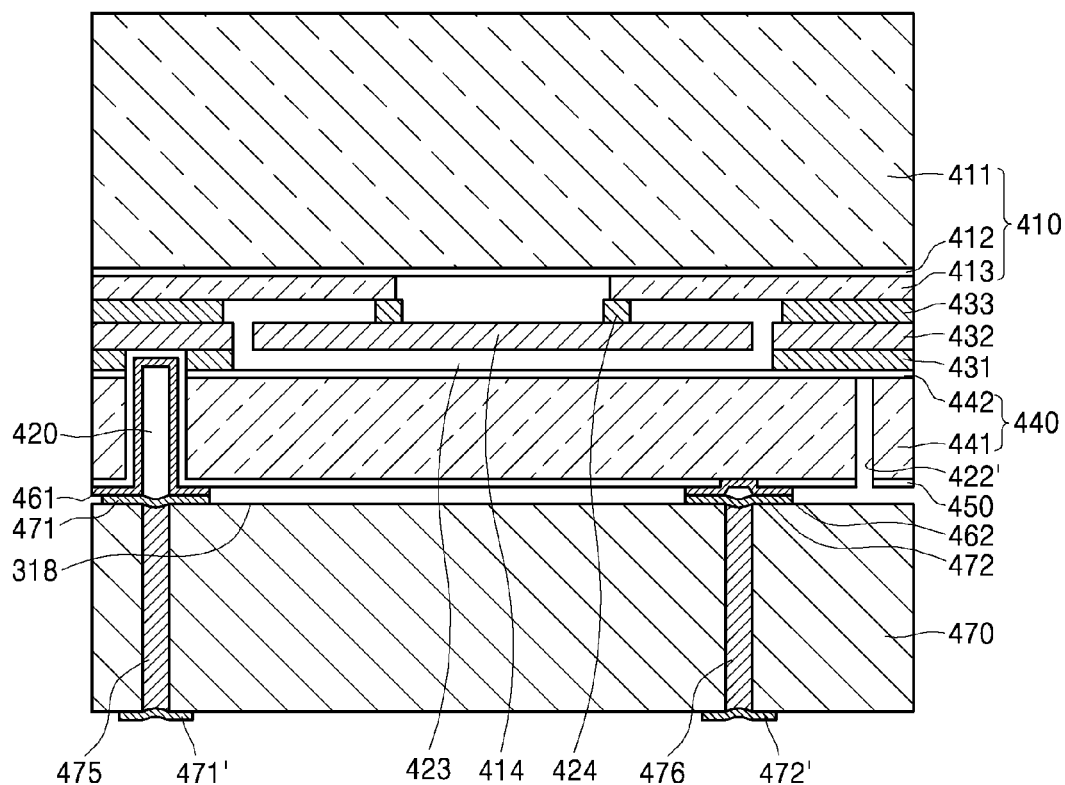

Referring to FIG. 25, a plurality of bonding pads formed on a pad substrate 470 is respectively bonded to the first and second electrode layers 461 and 462. The bonding pads include a first upper pad 471 and a second upper pad 472 that are disposed on an upper surface 318 of the pad substrate 470 and respectively bonded to the first and second electrode layers 461 and 462.

Figure 26:
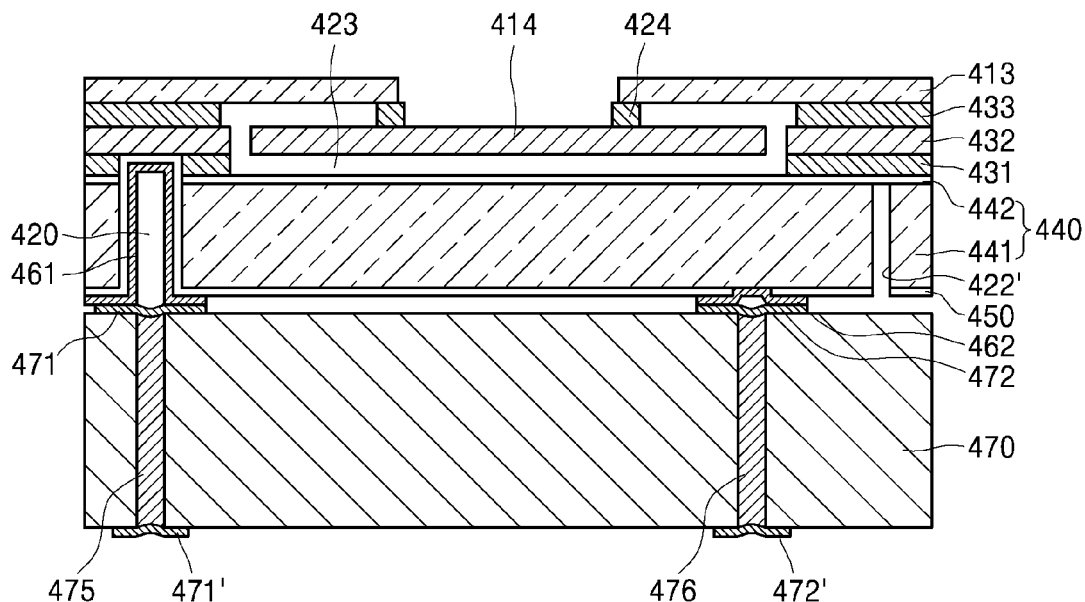

Referring to FIG. 26, the first lower substrate 411 and the first insulating layer 412 are removed. The first lower substrate 411 may be removed by, for example, a grinding and a plasma etching process, and the first insulating layer 412 may be removed by an ICP dry etching process.

Figure 27:
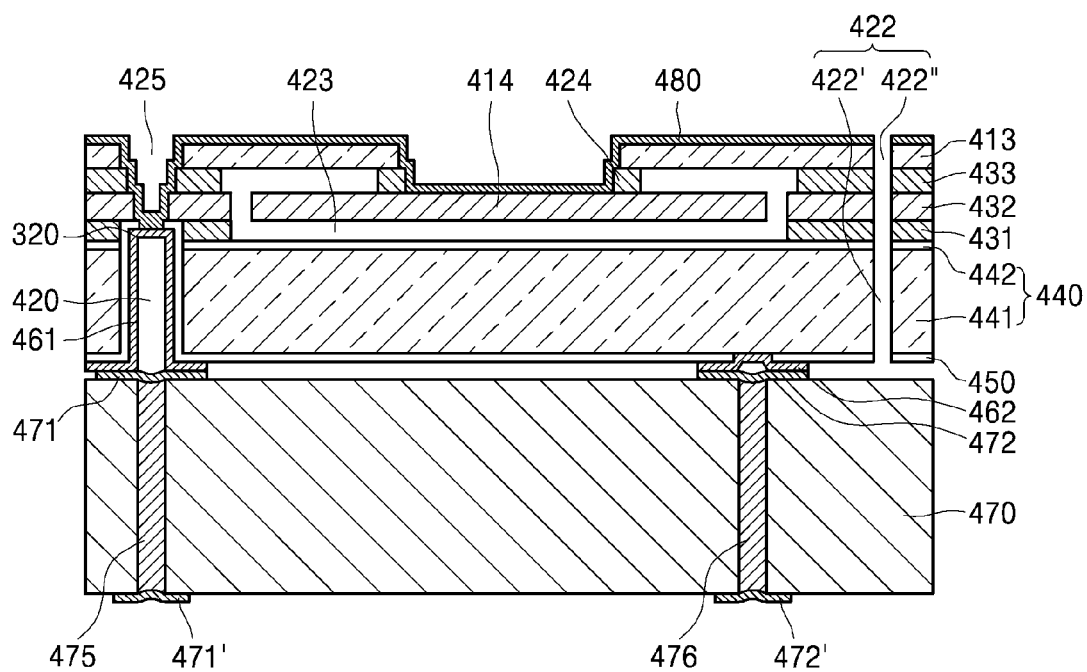

Referring to FIG. 27, a groove 425 exposing an upper surface 320 of the first electrode layer 461 is formed by etching the membrane 413, the first and second supports 433 and 432, and the lower insulating layer 450 above the via hole 420. For example, an upper electrode 480 is formed on an inner wall of the groove 425, the membrane 413, the bridge membrane 414, first support 433, second support 432, and upper portion 320 of the first electrode layer 461. Accordingly, the upper electrode 480 may be formed to contact the upper surface 320 of the first electrode layer 461. In addition, an upper trench 422" is formed to be connected to the lower trench 422' by etching the upper electrode 480, the membrane 413, the first, second, and third supports 433, 432, and 431, and the upper insulating layer 442. Accordingly, the trench 422 for preventing crosstalk may be formed through the upper electrode 480, the membrane 413, the first, second, and third supports 433, 432, and 431, the upper insulating layer 442, the upper substrate 441, and the lower insulating layer 450.

As described above, according to exemplary embodiments, generation of crosstalk between elements may be prevented by forming a trench penetrating through a conductive substrate in a CMUT having a structure in which the conductive substrate including the elements is bonded onto a pad substrate.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An ultrasonic transducer comprising: an upper substrate; a support disposed on an upper surface of the upper substrate and comprising a cavity; a membrane disposed on the support; a second electrode layer which is electrically connected to a lower surface of the upper substrate, and is separated from the first electrode layer laterally on the lower surface of the upper substrate and a trench formed by penetrating through the upper substrate and a lower insulating layer disposed on the lower surface of the upper substrate.

2. The ultrasonic transducer of claim 1, wherein the first electrode layer is disposed to cover a surface of the upper substrate and a surface of the support.

3. The ultrasonic transducer of claim 2, further comprising a via hole and an upper electrode,
wherein the first electrode layer is disposed to cover an inner wall of the via hole, and
wherein the upper electrode is disposed on the membrane and electrically connected to the first electrode layer.

4. The ultrasonic transducer of claim 1, further comprising a bridge membrane,
wherein the bridge membrane is connected to the membrane,
wherein the membrane comprises silicon, and
wherein the support comprises silicon oxide.

5. The ultrasonic transducer of claim 1, further comprising an upper insulating layer,
wherein the upper insulating layer is formed on the upper surface of the upper substrate, and
the lower insulating layer is patterned so that the second electrode layer contacts a portion of the lower surface of the upper substrate.

6. The ultrasonic transducer of claim 1, further comprising a first upper pad and a second upper pad,
wherein the first and second upper pads are disposed on the upper surface of the pad substrate and bonded respectively to the first electrode layer and the second electrode layer.

7. The ultrasonic transducer of claim 6, wherein the first and second electrode layers comprise at least one of gold (Au) and copper (Cu), and the first and second upper pads comprise at least one of Au, Cu, and tin (Sn).

8. The ultrasonic transducer of claim 6, wherein the bonding pads further comprise a first lower pad and a second lower pad that are disposed on a lower surface of the pad substrate and electrically connect to the first upper pad and the second upper pad.

9. An ultrasonic transducer comprising:
an upper substrate;
a support structure disposed on the upper substrate and comprising a cavity;
a membrane disposed on the support structure;
a bridge membrane connected to the membrane and separated from the support structure;
a first electrode layer disposed on the upper substrate;
a second electrode layer electrically connected to a lower surface of the upper substrate and is separated from the first electrode layer; and
an upper electrode disposed on the membrane and the bridge membrane to contact the first electrode layer.

10. The ultrasonic transducer of claim 9, wherein a via hole penetrates through the upper substrate, and
the first electrode layer covers an inner wall and an upper portion of the via hole.

11. The ultrasonic transducer of claim 10, further comprising a trench,
wherein the trench is formed by penetrating through the upper substrate and a lower insulating layer.

12. The ultrasonic transducer of claim 9, wherein the support structure comprises a third support, a second support, and a first support that are sequentially stacked on the upper substrate.

13. The ultrasonic transducer of claim 12, wherein the bridge membrane is disposed at a same level as that of the second support.

14. The ultrasonic transducer of claim 12, wherein the membrane and the bridge membrane are connected to each other via a bridge support.

15. The ultrasonic transducer of claim 9, further comprising an upper insulating layer and a lower insulating layer,
wherein the upper and lower insulating layers are respectively disposed on an upper surface and the lower surface of the upper substrate, and
wherein the lower insulating layer is patterned so that the second electrode layer contacts the lower surface of the upper substrate.

16. The ultrasonic transducer of claim 9, further comprising a first upper pad and a second upper pad,
wherein the first and second upper pads are disposed on an upper surface of the pad substrate and bonded respectively to the first electrode layer and the second electrode layer.

17. The ultrasonic transducer of claim 1, further comprising an upper electrode disposed on the membrane, and
another trench which is formed through the upper electrode, the membrane, and the support, and is joined with the trench.

* * * * *